(12) United States Patent
Miller et al.

(10) Patent No.: US 8,111,150 B2
(45) Date of Patent: Feb. 7, 2012

(54) PHYSIOLOGICAL DATA ACQUISITION AND MANAGEMENT SYSTEM FOR USE WITH AN IMPLANTED WIRELESS SENSOR

(75) Inventors: Donald J. Miller, Roswell, GA (US); Kim Rutkowski, Atlanta, GA (US); Jason Kroh, Villa Rica, GA (US); Shawn Michael Brogdon, Marietta, GA (US); Erik Moore, Roswell, GA (US)

(73) Assignee: CardioMEMS, Inc., Atlanta, GA (US)

( * ) Notice: Subject to any disclaimer, the term of this patent is extended or adjusted under 35 U.S.C. 154(b) by 417 days.

(21) Appl. No.: 11/852,724

(22) Filed: Sep. 10, 2007

(65) Prior Publication Data
US 2008/0081962 A1 Apr. 3, 2008

Related U.S. Application Data

(60) Provisional application No. 60/824,927, filed on Sep. 8, 2006.

(51) Int. Cl.
*G08B 1/08* (2006.01)
*G08B 23/00* (2006.01)
*H01Q 7/00* (2006.01)
*H03J 3/04* (2006.01)

(52) U.S. Cl. ............... 340/539.12; 340/573.1; 343/866; 334/5

(58) Field of Classification Search ............ 340/539.12, 340/573.3, 573.4, 539.11, 539.15; 334/1, 334/4–6, 8, 9; 600/9, 10, 12, 13; 343/866, 343/868, 873
See application file for complete search history.

(56) References Cited

U.S. PATENT DOCUMENTS

| | | | | |
|---|---|---|---|---|
| 2,512,641 A | * | 6/1950 | Halstead | 455/157.1 |
| 3,541,995 A | * | 11/1970 | Fathauer | 119/51.02 |
| 3,550,137 A | * | 12/1970 | Kuecken | 343/744 |
| 3,651,243 A | | 3/1972 | Homor et al. | |

(Continued)

FOREIGN PATENT DOCUMENTS

EP 2178166 A1 * 4/2010

(Continued)

OTHER PUBLICATIONS

International Search Report and Written Opinion, PCT/US07/078027, Feb. 11, 2008.

(Continued)

*Primary Examiner* — Jennifer Mehmood
(74) *Attorney, Agent, or Firm* — Kilpatrick Townsend & Stockton LLP

(57) ABSTRACT

Aspects and embodiments of the present invention provide a system for obtaining, processing and managing data from an implanted sensor. In some embodiments, a patient or other persons can use a flexible antenna to obtain data from the implanted sensor. The flexible antenna includes at least one transmit loop and at least one receive loop. The transmit loop is adapted to propagate energizing signals to the implanted sensor. The receive loop is adapted to detect a response signal from the implanted sensor. The transmit loop includes a capacitor formed by a discontinuous area. The capacitor is adapted to allow the loop to be tuned. The flexible antenna can communicate with a patient device that collects the data from the implanted sensor, creates a data file and transmits the data file to a remote server over a network. A physician or other authorized person may access the remote server using an access device.

22 Claims, 8 Drawing Sheets

U.S. PATENT DOCUMENTS

| | | | |
|---|---|---|---|
| 4,127,110 A | 11/1978 | Bullara | |
| 4,281,212 A | 7/1981 | Bogese | |
| 4,424,403 A | 1/1984 | Bogese | |
| 4,467,138 A | 8/1984 | Brorein | |
| 4,679,560 A | 7/1987 | Galbraith | |
| 5,043,531 A | 8/1991 | Gutenson et al. | |
| 5,153,583 A * | 10/1992 | Murdoch | 340/10.34 |
| 5,272,466 A * | 12/1993 | Venczel | 340/573.3 |
| 5,280,646 A * | 1/1994 | Koyama et al. | 455/300 |
| 5,313,953 A * | 5/1994 | Yomtov et al. | 600/508 |
| 5,491,299 A | 2/1996 | Naylor | |
| 5,574,470 A * | 11/1996 | de Vall | 343/895 |
| 5,673,054 A | 9/1997 | Hama | 343/744 |
| 5,701,121 A * | 12/1997 | Murdoch | 340/10.34 |
| 5,943,022 A * | 8/1999 | Massey | 343/744 |
| 5,976,070 A | 11/1999 | Ono | |
| 6,009,350 A * | 12/1999 | Renken | 607/32 |
| 6,025,725 A * | 2/2000 | Gershenfeld et al. | 324/652 |
| 6,111,520 A * | 8/2000 | Allen et al. | 340/870.16 |
| 6,208,305 B1 * | 3/2001 | King | 343/713 |
| 6,252,163 B1 | 6/2001 | Fujimori et al. | |
| 6,278,379 B1 | 8/2001 | Allen et al. | |
| 6,298,271 B1 * | 10/2001 | Weijand | 607/60 |
| 6,448,500 B1 | 9/2002 | Hosaka et al. | |
| 6,680,708 B2 * | 1/2004 | Yamaki | 343/741 |
| 6,777,940 B2 | 8/2004 | Macune | |
| 6,822,570 B2 | 11/2004 | Dimmer et al. | |
| 6,837,438 B1 * | 1/2005 | Takasugi et al. | 235/492 |
| 6,855,115 B2 | 2/2005 | Fonseca et al. | |
| 6,870,105 B2 | 3/2005 | Maydanich et al. | |
| 6,885,354 B2 * | 4/2005 | Takei | 343/870 |
| 6,895,281 B1 * | 5/2005 | Amundson et al. | 607/60 |
| 6,898,454 B2 * | 5/2005 | Atalar et al. | 600/410 |
| 6,943,688 B2 * | 9/2005 | Chung et al. | 340/572.7 |
| 7,049,523 B2 | 5/2006 | Shuman et al. | |
| 7,208,684 B2 | 4/2007 | Fetterolf et al. | |
| 7,215,991 B2 * | 5/2007 | Besson et al. | 600/509 |
| 7,439,723 B2 | 10/2008 | Allen et al. | |
| 7,466,120 B2 | 12/2008 | Miller et al. | |
| 7,498,799 B2 | 3/2009 | Allen et al. | |
| 7,550,978 B2 | 6/2009 | Joy et al. | |
| 7,679,355 B2 | 3/2010 | Allen et al. | |
| 2003/0028094 A1 * | 2/2003 | Kumar et al. | 600/410 |
| 2003/0085799 A1 * | 5/2003 | Ghabra et al. | 340/5.72 |
| 2004/0036626 A1 * | 2/2004 | Chan et al. | 340/870.17 |
| 2004/0122494 A1 * | 6/2004 | Eggers et al. | 607/103 |
| 2004/0135726 A1 * | 7/2004 | Shamir et al. | 343/700 MS |
| 2004/0164864 A1 * | 8/2004 | Chung et al. | 340/572.7 |
| 2004/0178958 A1 * | 9/2004 | Kadambi et al. | 343/700 MS |
| 2004/0236209 A1 | 11/2004 | Misic et al. | |
| 2005/0075697 A1 | 4/2005 | Olson et al. | |
| 2005/0099341 A1 * | 5/2005 | Zhang et al. | 343/700 MS |
| 2006/0001583 A1 * | 1/2006 | Bisig | 343/718 |
| 2006/0047327 A1 * | 3/2006 | Colvin et al. | 607/60 |
| 2006/0178586 A1 * | 8/2006 | Dobak | 600/508 |
| 2006/0244465 A1 | 11/2006 | Kroh et al. | |
| 2007/0118038 A1 * | 5/2007 | Bodecker et al. | 600/486 |
| 2007/0181331 A1 | 8/2007 | Kroh et al. | |
| 2007/0185546 A1 * | 8/2007 | Tseng et al. | 607/60 |
| 2007/0222603 A1 * | 9/2007 | Lai et al. | 340/572.7 |
| 2008/0029590 A1 * | 2/2008 | Zosimadis et al. | 235/375 |
| 2008/0061955 A1 * | 3/2008 | Tang et al. | 340/447 |
| 2008/0078567 A1 | 4/2008 | Miller et al. | |
| 2008/0081962 A1 * | 4/2008 | Miller et al. | 600/301 |
| 2008/0278391 A1 * | 11/2008 | Mayer | 343/725 |
| 2009/0033486 A1 * | 2/2009 | Costantino | 340/540 |
| 2009/0224773 A1 * | 9/2009 | Joy et al. | 324/633 |
| 2009/0278553 A1 | 11/2009 | Kroh et al. | |

FOREIGN PATENT DOCUMENTS

| | | |
|---|---|---|
| WO | WO 2007/008493 A | 1/2007 |

OTHER PUBLICATIONS

Non-Final Office Action mailed Mar. 29, 2007, U.S. Appl. No. 11/479,527, U.S. Patent No. 7,432,723.

Response to Non-Final Office Action filed Jul. 26, 2007, U.S. Appl. No. 11/479,527, U.S. Patent No. 7,432,723.

Notice of Allowance mailed Mar. 27, 2008, U.S. Appl. No. 11/479,527, U.S. Patent No. 7,432,723.

Request for Continued Examination filed May 15, 2008, U.S. Appl. No. 11/479,527, U.S. Patent No. 7,432,723.

Notice of Allowance mailed May 23, 2008, U.S. Appl. No. 11/479,527, U.S. Patent No. 7,432,723.

Supplemental Notice of Allowance mailed Aug. 12, 2008, U.S. Appl. No. 11/479,527, U.S. Patent No. 7,432,723.

Chirlian, Basic Network Theory, McGraw Hill Book Co., 1969, Impedance section: pp. 275-283, 350-355.

* cited by examiner

PHYSIOLOGICAL DATA ACQUISITION AND MANAGEMENT SYSTEM FOR USE WITH AN IMPLANTED WIRELESS SENSOR

RELATED APPLICATIONS

This application claims priority to U.S. Provisional Application No. 60/824,927, filed Sep. 8, 2006, the contents of which is incorporated herein by reference.

This application is related to U.S. patent application Ser. No. 11/479,395, filed Jun. 30, 2006, which claims priority to U.S. Provisional Application No. 60/697,867, filed Jul. 8, 2005; U.S. Provisional Application No. 60/697,878, filed Jul. 8, 2005 and U.S. Provisional Application No. 60/707,094, filed Aug. 10, 2005, the contents of each of which is incorporated herein by this reference.

FIELD OF THE INVENTION

This invention relates generally to a system for communicating physiological data obtained from a wireless sensor over a network, and in particular to a flexible coupling loop for communicating with a wireless sensor implanted within a body and a client device which in turn communicates with a remote server over a network.

BACKGROUND OF THE INVENTION

Wireless sensors can be implanted within the body and used to monitor physical conditions, such as pressure or temperature. These sensors can be used to monitor physical conditions within the heart or an abdominal aneurysm. An abdominal aortic aneurysm (AAA) is a dilatation and weakening of the abdominal aorta that can lead to aortic rupture and sudden death. In the case of a repaired abdominal aneurysm, a sensor can be used to monitor pressure within the aneurysm sac to determine whether the intervention is leaking. The standard treatment for AAAs employs the use of stent-grafts that are implanted via endovascular techniques. However, a significant problem that has emerged with these stent-grafts for AAAs is acute and late leaks of blood into the aneurysm's sac. Currently, following stent-graft implantation, patients are subjected to periodic evaluation via abdominal CT (Computed Tomography) with IV contrast to identify the potential presence of stent-graft leaks. This is an expensive, risky procedure that lacks appropriate sensitivity to detect small leaks.

Typically, the sensors utilize an inductive-capacitive ("LC") resonant circuit with a variable capacitor. The capacitance of the circuit varies with the pressure of the environment in which the sensor is located and thus, the resonant frequency of the circuit varies as the pressure varies. Thus, the resonant frequency of the circuit can be used to calculate pressure.

Ideally, the resonant frequency is determined using a non-invasive procedure. The signal from the sensor is weak relative to the signal used to energize the sensor, but is the same frequency and dissipates quickly. In one embodiment, the difference between the signals is on the order of 150 dB and the sensor signal is sampled approximately 35 nanoseconds after the energizing signal is turned off. In order to communicate with the sensor, the system uses a coupling loop and a cable assembly. For example, a person with an implanted sensor may lie, sit, or stand close to or in contact with a flexible antenna or coupling loop. Due to the unique characteristics of the transmitted and received signals the coupling loop and the cable assembly need to isolate the energizing signal and the sensor signal, support the necessary sampling speed, and support a relatively large bandwidth.

Some antennas or coupling loops use a capacitor soldered to the antenna to reduce mismatch losses. One problem with this approach is that the antenna may be flexed by the patient's weight and in some embodiments the solder joint may break or otherwise become inoperable. Accordingly, a need exists for a flexible antenna that meets the bandwidth requirement for communicating with a sensor implanted into a body that can withstand the patient's weight without breaking.

Some patients may need to have data retrieved from the implanted sensors relatively often. Conventional systems require the patient to come to the hospital to obtain and process data from the implanted sensor. Accordingly, a need exists for a data management system that can communicate implanted sensor data and/or processed data to a remote server and allow a physician or other individual to read and analyze the data.

BRIEF SUMMARY OF THE INVENTION

Aspects and embodiments of the present invention provide a system for obtaining, processing and managing data from an implanted sensor. In some embodiments, a patient or other persons can use a flexible antenna to obtain data from the implanted sensor. The flexible antenna can communicate with a patient device that collects the data from the implanted sensor, creates a data file and transmits the data file to a remote server over a network. A physician or other authorized person may access the remote server using an access device.

In some embodiments of the present invention, the flexible antenna includes at least one transmit loop and at least one receive loop made from a conductive material and mounted on a flexible substrate. The transmit loop is adapted to propagate energizing signals to the implanted sensor. The receive loop is adapted to detect a response signal from the implanted sensor. The transmit loop includes a capacitor integrated into the at least one loop. The capacitor is adapted to allow the loop to be tuned. In one embodiment, the transmit loop is discontinuous in one or more locations. The discontinuous portions can include areas that overlap. The overlapping areas may be spaced at pre-determined distances creating a capacitor. In one embodiment of the present invention, the antenna loop elements are essentially planar. In another embodiment, the antenna loop elements are essentially tubular.

In some embodiments of the present invention, the patient device is a processor-based device with a network connector and an output to, for example, prompt the patient to reposition themselves or personnel to reposition the antenna to allow the antenna to correctly communicate with the implanted sensor.

In some embodiments of the present invention, the remote server is a processor-based device having a management engine that can scan for new data files, format data into databases, generate a data file waveform, and/or send notifications and other data to physicians or authorized persons. The physician or authorized persons can access the remote server over a network using an access device.

An advantage of some embodiments of the present invention includes allowing for patients to orient themselves, with or without the assistance of medical personnel, in a desired position, such as sitting or standing, to obtain a sensor signal.

A further advantage of some embodiments of the present invention is allowing the antenna to be used in a variety of angles relative to a person.

A further advantage of some embodiments of the present invention is providing a pad having built in shielding to reduce environmental effects from room objects, such as bed springs and heating blankets.

A further advantage of some embodiments of the present invention is providing a pad adapted to receive a person's head and allowing a patient to position in an optimal position relative to an antenna for receiving signals from implanted sensor circuits.

A further advantage of some embodiments of the present invention is providing an antenna circuit that can automatically provide self-diagnostic signals to promote accurate performance of the antenna.

A further advantage of some embodiments of the present invention is providing an antenna circuit that includes a switch to prevent the circuit from interfering with normal operation of the antenna.

A further advantage of some embodiments of the present invention is using a radiopaque marker, such as the implanted sensor circuit or logo, cross, or set of cross-hairs, to orient the antenna relative to an implanted sensor circuit.

BRIEF DESCRIPTION OF THE DRAWINGS

FIG. 5b is a side view of the antenna assembly of FIG. 5a.

DETAILED DESCRIPTION OF THE INVENTION

Figure 1:
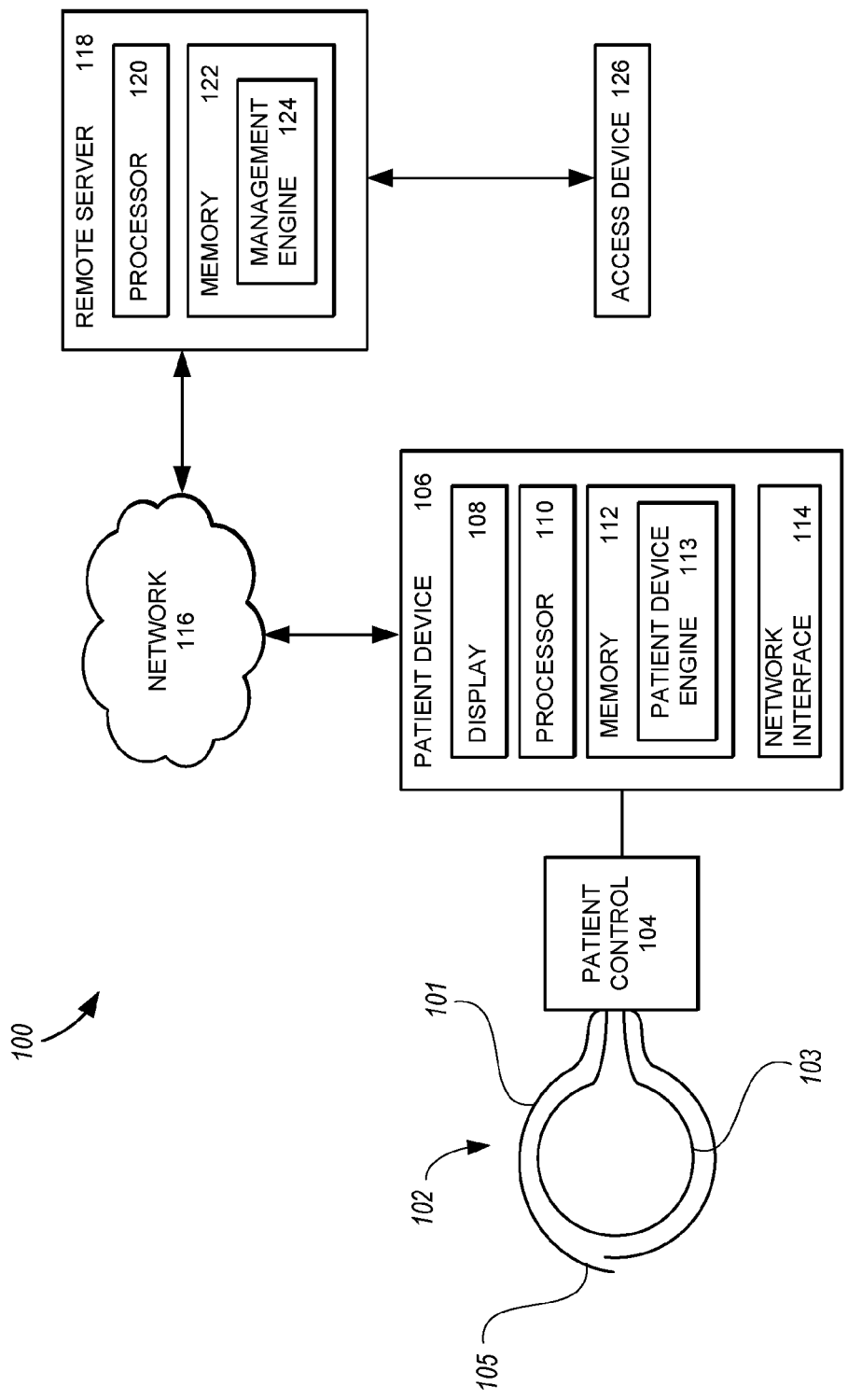
FIG. 1 illustrates a data management system according to one embodiment of the present invention.

Certain aspects and embodiments of the present invention provide a data acquisition and management system for patients with an implanted sensor device. The system provides the ability to acquire data from the implanted sensor device and transmit data to a remote server that is accessible by physicians or other authorized users. FIG. 1 illustrates one embodiment of the data acquisition and management system 100. The system 100 includes an acquisition device such as an antenna 102. The antenna 102 includes a transmit loop 101 and a receive loop 103. The transmit loop 101 may include a discontinuous area 105 that can form a capacitor, as described below. The antenna 102 can include any number of loop elements and, in some embodiments, the receive loop element 103 may include a capacitor, either soldered to the receive loop or formed using the receive loop.

The antenna 102 may connect to a patient control device 104 over wires, wirelessly or otherwise. The patient control device 104 may allow the patient to initiate interrogation of the implanted sensor. For example, the patient control device 104 may include a button that, when pushed, depressed, or otherwise activated, commands the patient control device 104 to transmit an energizing signal to the implanted sensor.

The antenna 102 and/or patient control device 104 may also be in communication with a patient device 106. The patient device 106 may monitor various activities of acquiring data from the implanted sensor, such as by monitoring the existence and strength of the energizing and implanted sensor signal and include a display 108 to display instructions, status of data acquisition or other information to the patient. As illustrated in FIG. 1, the patient control device 104 may be separate from the patient device 106. In some embodiments, the patient device 106 includes the patient control device 104. In other embodiments, the antenna 102 includes the patient control device 104. The patient device 106 also includes a processor 110 and a computer-readable memory, such as memory 112. Memory 112 may include executable code, such as a patient device engine 113. The patient device engine 113 may be adapted to receive data from the antenna 102, display instructions or other information on the display 108, convert data to digital data and/or format implanted sensor data into a data file to send over a network. The implanted sensor data and/or data file may be stored in memory 112. The data file may include information in addition to the implanted sensor data. Additional information can include patient identification and implanted sensor signal waveform data. For example, the patent device engine 113 can create sensor signal waveforms from the implanted sensor data. The antenna 102, patient control device 104, and patient device 106 may be located in and/or outside a hospital or other medical facility. For example, these devices may be located at the patient's home.

The patient device 106 also includes a network interface 114, such as an Ethernet port, modem port or other network port adapter. The network interface 114 is adapted to connect to network 116 and to send the data file to a remote server 118 over the network 116. The network 116 may include one or a combination of any type of network such as LAN, WAN, WLAN, public switched telephone network, GSM, or otherwise. The remote server 118 receives the data file and includes a processor 120 and a computer-readable memory, such as memory 122. Memory 122 can store the data file and includes computer-executable code, such as a management engine 124. The management engine 124 may periodically, such as once per minute, scan the data files stored in the memory 122 to determine whether new or additional data is in the memory 122. In some embodiments, the management engine 124 can format the data file into various forms and notify pre-determined authorized persons on a user list stored in the memory 122, such as by electronic mail, that a new data file is present and ready for review. Formatting the data file may include sorting the data into a database, generating a waveform, and creating a visual display of the data, such as by creating a jpeg file.

Physicians or authorized persons may use an access device 126, such as a computer system, to access the data file and/or formatted data in the remote server memory 122. For example, the access device 126 may access a web interface that authenticates the access device users and allows the users to view and manage the patient data, view patient data histories, set automatic alert ranges to alert the authorized user when the patient data exceeds set levels, or any other function associated with viewing, managing, and analyzing the data file. Accordingly, embodiments of the present invention allow patients to stay at home while the system monitors signals from the implanted sensors and provides medical personnel in a remote location with access to the data.

In some embodiments of the present invention, the patient device 106 may be remotely configured or updated from the access device 126 through the network 116. For example, additional software or software updates may be sent over the network 116 and installed onto the patient device 106 using the access device 126 or other device connected to, and communicating through, the network.

In some embodiments of the present invention, the patient device memory 112 may store the implanted sensor data and/or data file. The patient device 106 may be in communication with a data storage system, directly or through a local network, to store the sensor data and/or data file. For example, if the network 116 failed, the patient device memory 112 and/or data storage system may provide a back-up storage to data stored on the remote server 118.

Figure 2:
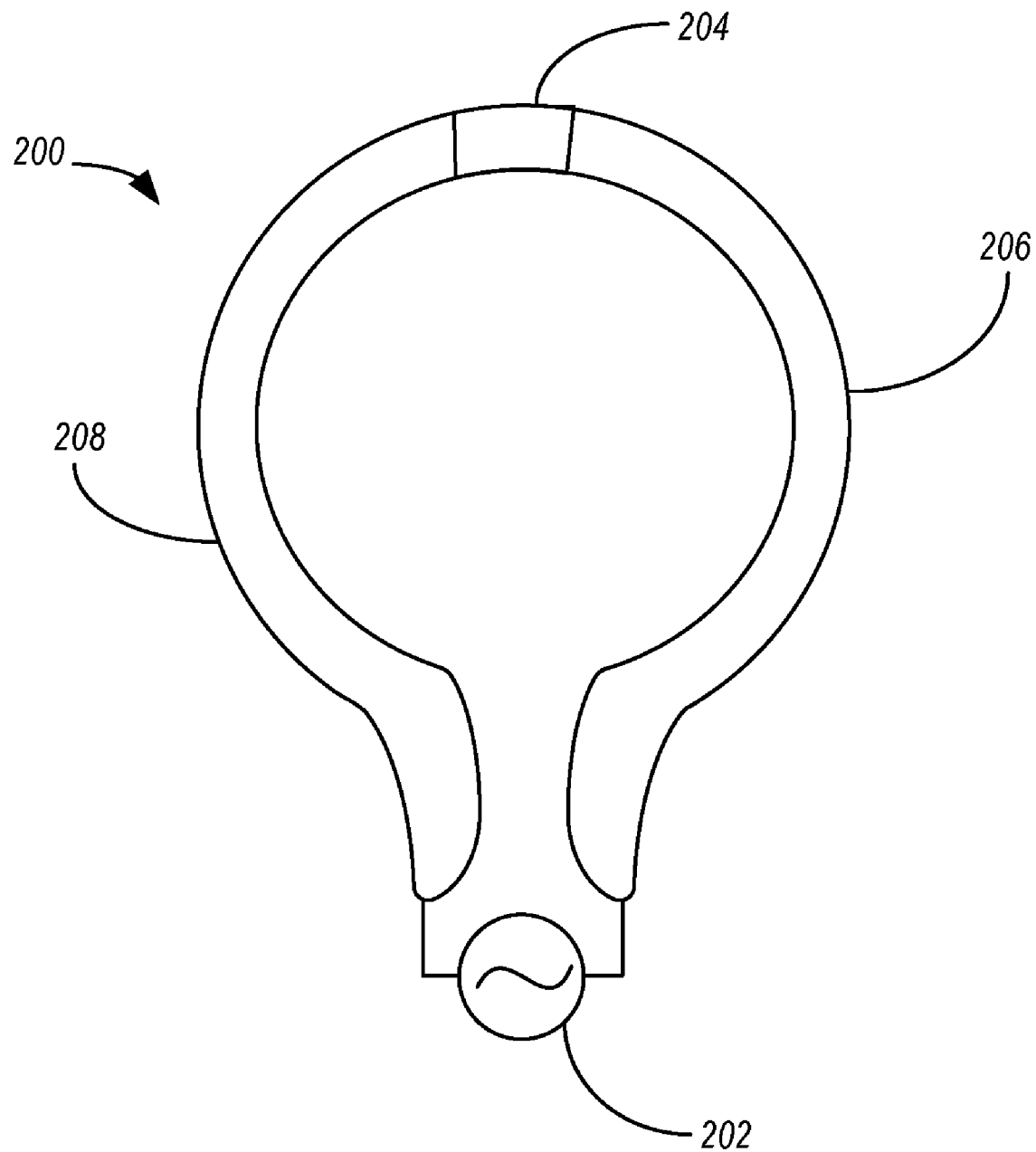
FIG. 2 illustrates a transmit loop according to one embodiment of the present invention.
Figure 3:
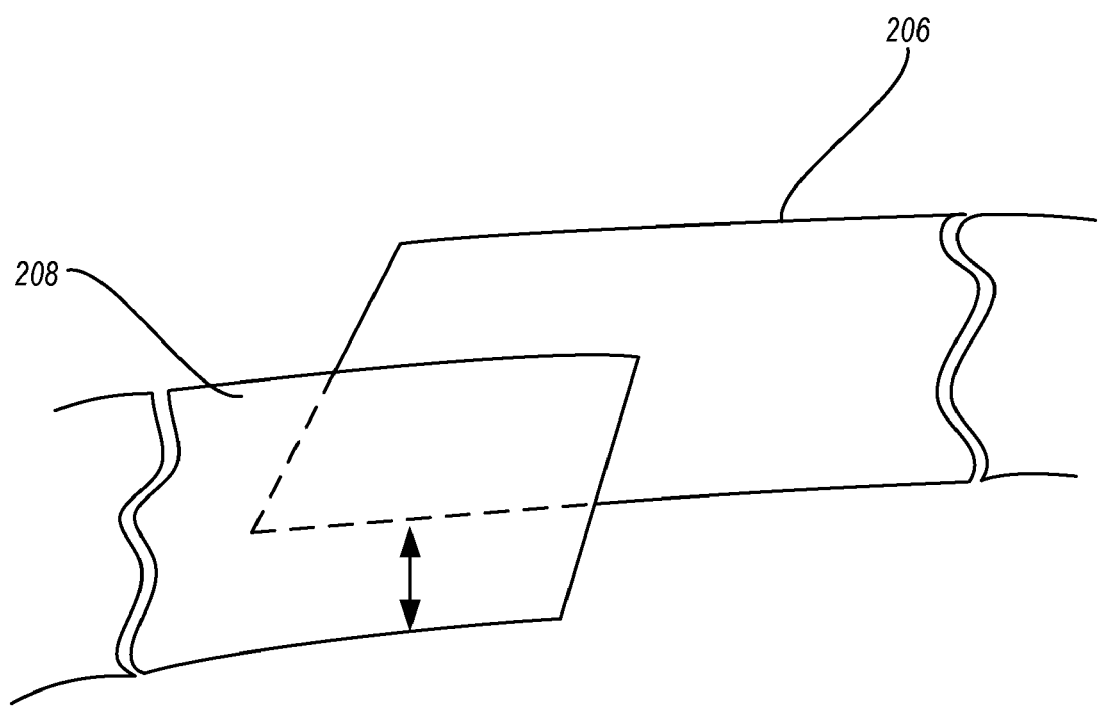
FIG. 3 illustrates a discontinuous area of the transmit loop of FIG. 2.
Figure 4:
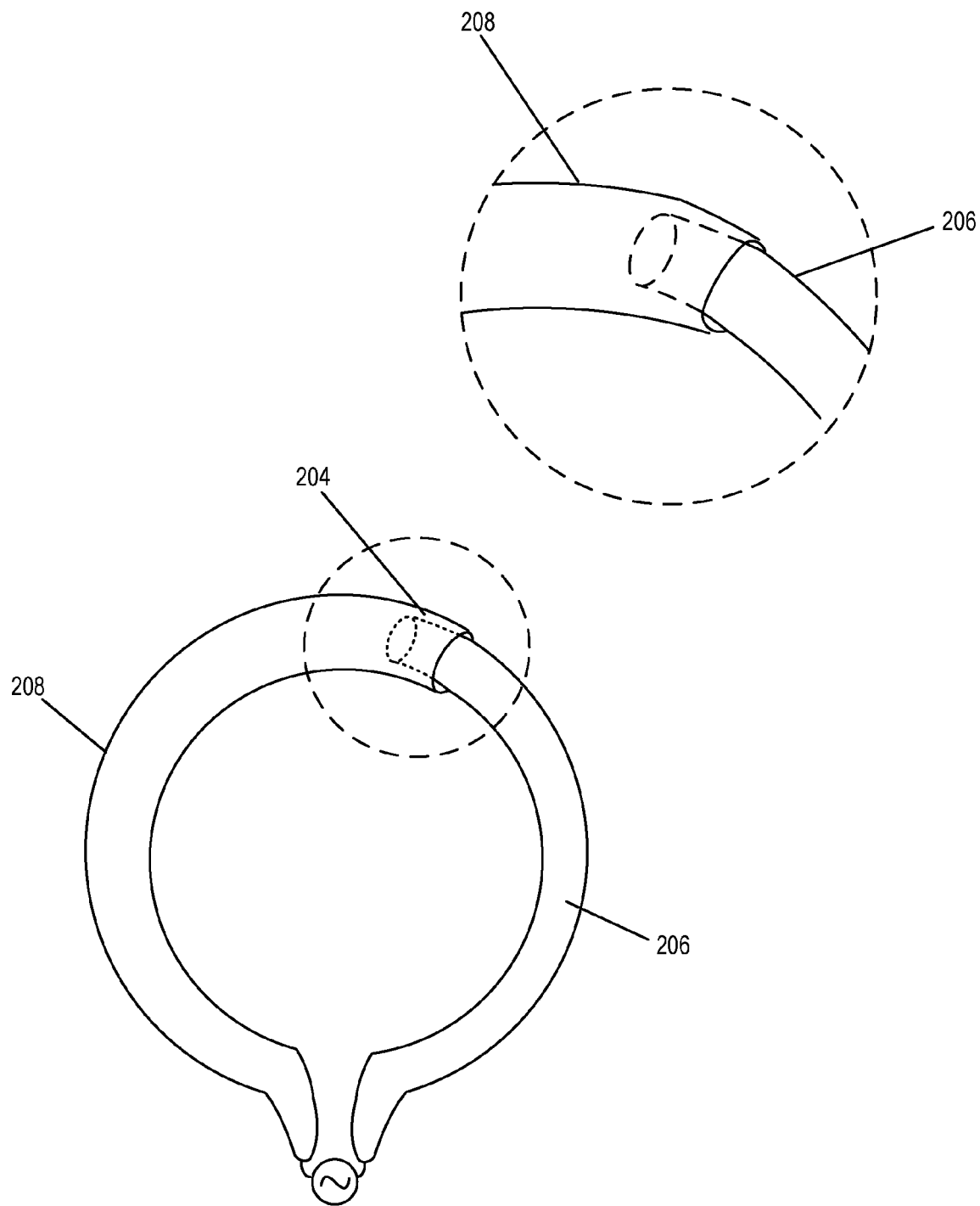
FIG. 4 illustrates a tubular transmit loop according to one embodiment of the present invention.

FIG. 2 illustrates one embodiment of one antenna loop 200. The antenna loop 200 may connect to a transmitter 202 and transmit a signal to the implanted sensor. The antenna loop 200 can include one or more discontinuous areas 204 that form a capacitor to decrease or eliminate mismatch losses. The discontinuous area 204 may include an area where two or more loop element portions 206, 208 do not physically connect but overlap each other. The loop element portions 206, 208 may be relatively flat or planar, tubular, as illustrated in FIG. 4, or any other shape. The discontinuous area 204 may include a space or gap, as illustrated in FIG. 3, between the two loop element portions 206, 208. The size of the space or gap, i.e. the distance between the two loop element portions 206, 208, may be pre-set depending on the desired capacitance. In some embodiments, the space or gap is filled with air. In other embodiments, the space or gap may be filled with other dielectric materials, such as materials that do not conduct electricity with relative ease. The loop element portions 206, 208 may be made from any type of conductive material, such as cooper, and configured to any shape. For example and as illustrated in FIG. 4, the loop element portions 206, 208 may be essentially tubular.

Figure 5A:
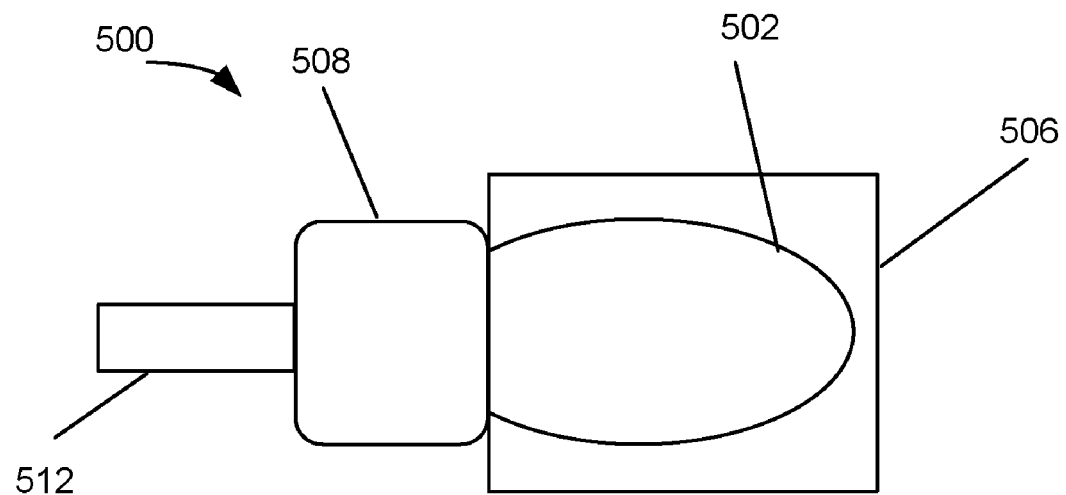
FIG. 5a is a top view of an antenna assembly according to one embodiment of the present invention.
Figure 5B:
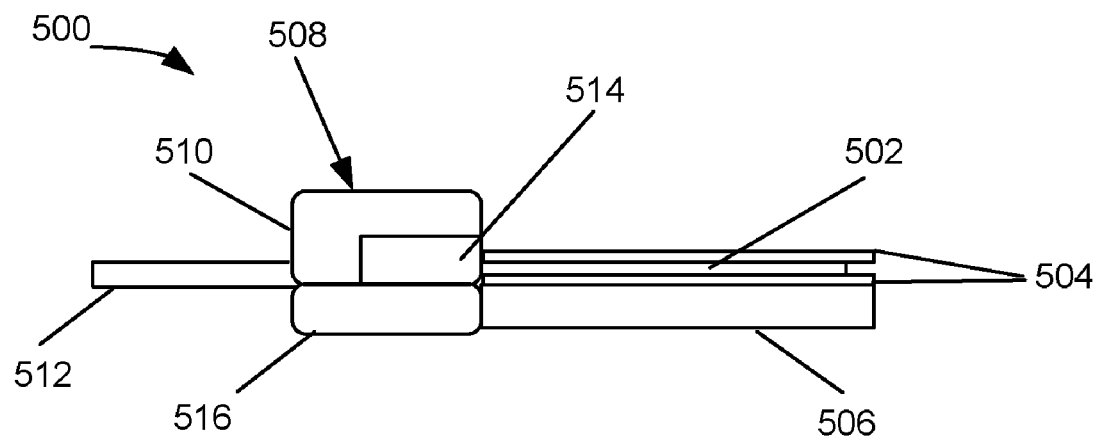

Antenna loops according to various embodiments of the present invention may be combined with one or more other antenna loops, such as a receiver loop, and connected to a substrate, such as plastic or other material that allows radio waves to pass through the substrate, to form an antenna assembly for an implanted sensor data acquisition and management system. FIGS. 5a and 5b illustrate one embodiment of a antenna assembly 500 that includes a flexible antenna 502. The antenna assembly 500 can be formed by locating the flexible antenna 502, such as a conductive material, between a protective covering, such as a sheath 504. The sheath 504 can include two portions, between which the flexible antenna 502 is located, and can be made of any material that is adapted to allow electromagnetic signals to pass through. In some embodiments of the present invention, the sheath 504 can be rubber that protects the flexible antenna 502 from becoming damaged or contacting conductive surfaces during use. One portion of the sheath 504 may be made from a different material or have a different color than the other portion. For example, one portion of the sheath 504 may be made from a clear polymer material, such that a user can view the flexible antenna 502, but the sheath portion protects the flexible antenna from damage.

One portion of the sheath can be connected to a substrate 506. The substrate 506 may be any material that is adapted to provide support to the sheath 504 and flexible antenna 502 and that allows electromagnetic signals to pass through. The substrate 506 and, optionally, the sheath 504 can be connected to a base 508. The base 508 can include a pad 510 and, as described in more detail below, a shield 514, and a support structure 516. In some embodiments, the base 508 can include a conduit through which a cable 512 connects to the flexible antenna 502. The pad 510 may be a headrest pad that includes soft material and is adapted to receive a person's head.

Figure 6:
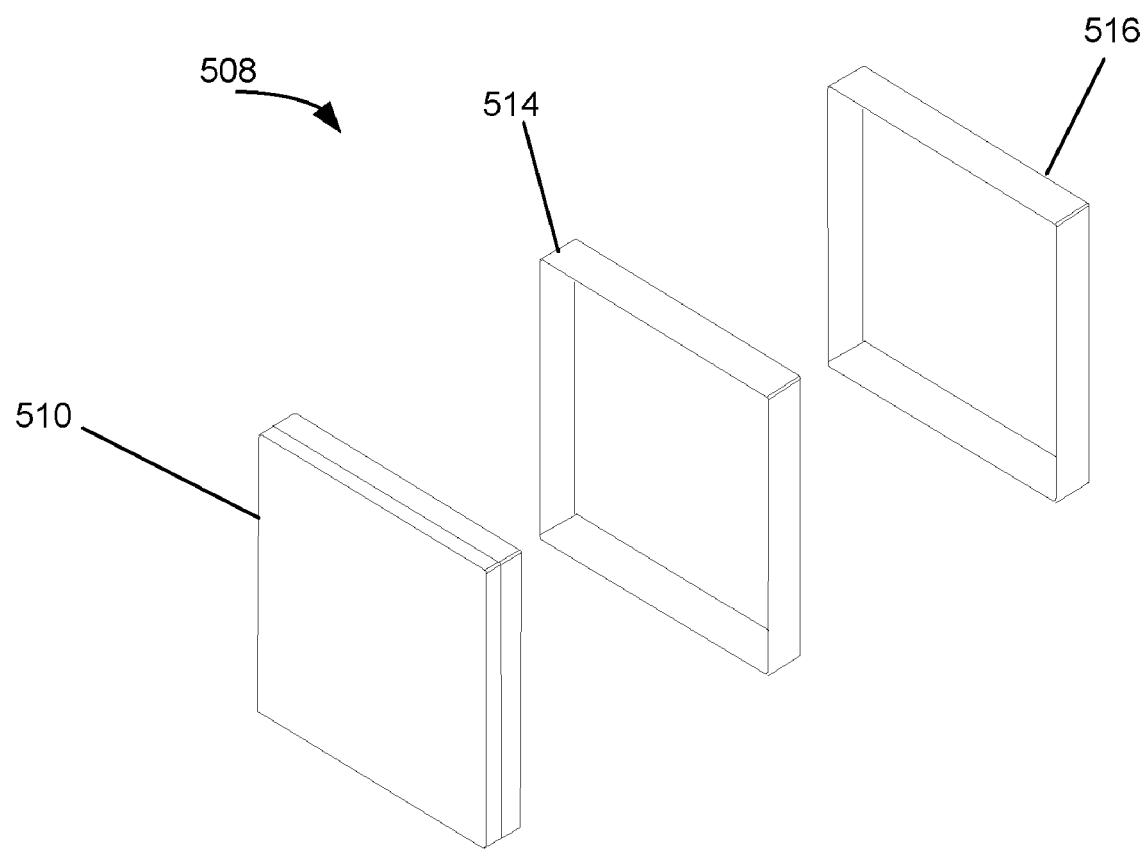
FIG. 6 is an exploded view of a base of an antenna assembly according to one embodiment of the present invention.

FIG. 6 illustrates one embodiment of the construction of a base 508. The base can include the pad 510 made from a foam material to provide a person using the antenna assembly 500 with a relatively comfortable structure on which to lay their head or other body part. The pad 510 may be attached to shield 514 that can include the conduit through which the cable 512 connects to the flexible antenna 502. The shield 514 may be adapted to include other electronic components, as necessary, and be made from a material that prevents, or substantially prevents, electromagnetic signals from passing through the shield 514. For example, the shield 514 can provide electromagnetic shielding from environmental signals such as EMI from other devices, reflections from the transmitted signal, or retransmitted resonances from tuned conductor lengths. This same shielding material may be attached to four sides of the base 508. An example of material of which the shield 514 may be made includes Zelt fabric. The shield 514 can be attached to a support structure 516. The support structure 516 can provide the base 508 with support to withstand repeated uses of the antenna assembly 500. In some embodiments, the support structure 516 can house additional electronics. Examples of material of which the support structure 516 can be made include vinyl, polymers, and metal. The pad 510 can be attached to the shield 514 and the shield 514 can be attached to the support structure 516 by any material. Examples of such material include glue, nails, screws, hooks, Velcro, and metallic and polymer connectors. The base 508 can be covered by an easily washable cover.

Figure 7:
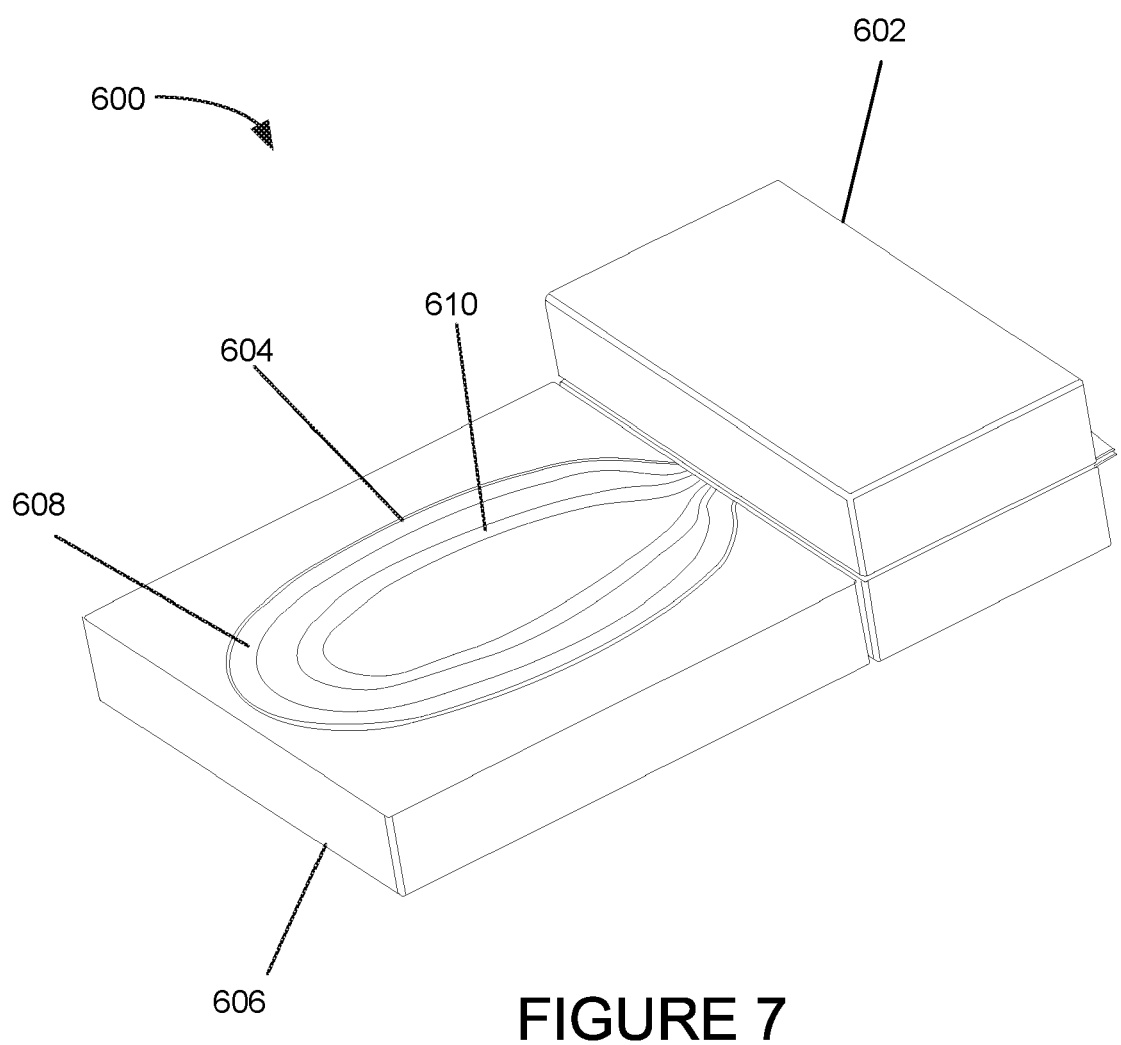
FIG. 7 is a perspective view of an antenna assembly according to one embodiment of the present invention.

FIG. 7 shows another embodiment of an antenna assembly 600. The antenna assembly 600 includes a pad 602 that may be a headrest pad adapted to allow a person to rest their head or other body part on the pad 602 while using the antenna assembly 600. The antenna assembly 600 also includes an antenna 604 attached to a substrate 606. The substrate 606 and, optionally, the antenna 604 may be attached to the pad 602. The antenna 604 can include a transmit loop 608 and receive loop 610. The transmit loop 608 may transmit energizing signals to a sensor and the receive loop 610 may receive sensor signals. The antenna 604 can be connected to electronics housed in the pad 602.

Embodiments of the flexible antenna, as illustrated in FIG. 5a, FIG. 5b and FIG. 7, may be made of copper foil attached to a polyimide (Kapton) flex material that is terminated to a standard FR-4 printed circuit board (PCB). The PCB can be encased in a stainless steel enclosure for protection and strength. This enclosure can be embedded in the pad. The exposed Kapton that can extend outside the pad can be sheathed by a thin layer of an FDA-compliant rubber (silicone or equivalent medical grade rubber). The antenna assembly may rest on a foam base pad with shielding material attached to the bottom of the pad. The patient may be able to cover this assembly with a bed sheet or large pillow cover. A cable can connect the antenna to a patient device or other device for communication between the patient or other device and the antenna. In some embodiments, the antenna can communicate wirelessly with the patient device or other device.

Flexible antennas according to various embodiments of the present invention can be used to interrogate the implanted sensor. Magnetic fields originating at the antenna energize the sensor with a low duty cycle, gated bursts of RF energy having a predetermined frequency or set of frequencies and a predetermined amplitude. Since the sensor is an inductive-capacitive (LC) resonator, the energy coupled from the antenna will continue to oscillate after the transmit signal is turned off. Once the antenna is gated off, the antenna will receive the ring down response from the sensor through inductive coupling.

The antenna may be relatively flat and flexible which will allow the user to lie on the antenna rather than maneuvering a relatively heavy wand. Since interrogation is through inductive coupling, the optimal orientation of the loop of the antenna with respect to the coil of the sensor is essentially parallel. Deviations may decrease the signal strength (effective inductive coupling) by the cosine of the angle. Flexibility of the antenna allows the user to wrap the antenna around parts of the body or with the use of positioning pads to achieve angles that would be difficult to achieve with a rigid antenna. The pad may be a headrest that is configured or shaped to assist the patient with the proper positioning. The length of the antenna may be selected to cover the typical interrogation area. In some embodiments of the present invention, the length of the antenna may be between 6 and 48 inches. In other embodiments, the length of the antenna may be between 12 and 22 inches. The length and width of the antenna according to various embodiments of the present invention may be optimized for different sensor types, the physical location of the implanted sensor, and human body physiological constraints. For example, monitoring of sensors placed in abdominal aortic aneurysms in an operating room environment may require an antenna of a length suitable for providing reliable communication with the sensor for patients of various heights, where the use of a similar antenna in a pad used for home monitoring of abdominal aortic aneurysm, congestive heat failure or other ailment may be of a shorter length—since the patient is able to move around to obtain a satisfactory reading.

In some embodiments, the antenna may be used to transmit and receive signals of between 30 and 37.5 MHz. The length and size of the antennas can be selected from a broad range of sizes to operate with the selected band, while the capacitor included with at least one antenna element can be tune to compensate for varying antenna sizes.

Figures 8A, 8B:
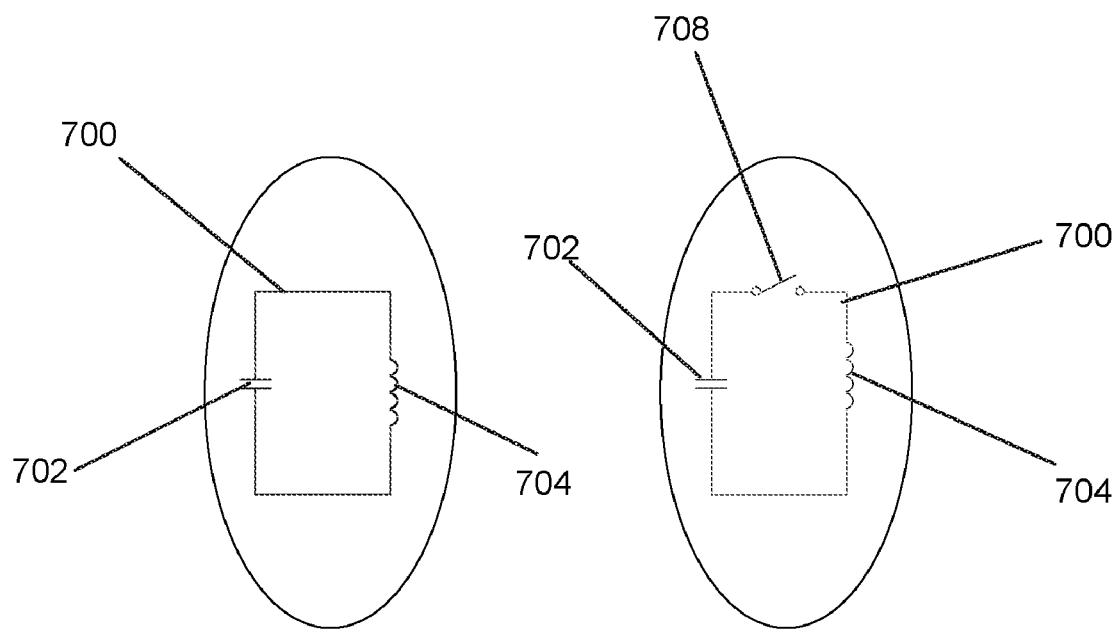
FIG. 8a is a schematic view of an antenna circuit according to one embodiment of the present invention.
FIG. 8b is a schematic view of the antenna circuit of FIG. 8a with an open switch.

Various embodiments of the present invention provide an antenna system that can perform self diagnostics to ensure accurate operation over time as well as wear. In one embodiment, a circuit can be embedded in the antenna which will resonate at a particular known frequency. The system can use this resonance as a check to ensure proper operation. For example, the system can detect the signal from the embedded circuit and compare the resonant frequency from that signal with a stored resonant frequency of the circuit. If deviations between the two resonant frequencies exist more than a preset threshold, the system can notify a user that a problem exists within the system. The system may also be able to check against the signal strength. Since the embedded circuit could interfere with the sensor circuit's signal, in one embodiment, the circuit can be designed to resonate slightly out of band. In another embodiment, the circuit can be designed with a switch that would effectively disable the resonance. FIGS. 8a and 8b illustrate one embodiment of an antenna circuit 700. The antenna circuit 700, which includes a capacitor 702 and an inductor 704, can be placed in proximity to, or within the circumference of, an antenna coil 706. The antenna circuit 700 may also include a switch 708 that can be switched on to conduct self-diagnostic operations, as shown in FIG. 8a, and switched off, as shown in FIG. 8b, if for example the circuit 700 interferes with the normal operation of the antenna.

Antennas according to various embodiments of the present invention may be used in the catheter lab or operating room during implantation procedures. During these procedures, the physician may use fluoroscopic imagining which helps facilitate the procedure. The antenna can be placed under the patient and will be used for calibration and for intra-procedure readings. Locating the antenna with respect to the sensor using fluoroscopy may be necessary to ensure that the sensor is within the interrogation region of the antenna. The antenna may need radiopaque markers to ensure proper location. These radiopaque markers could include a cross, bull's eye, logo, lettering, etc.

The foregoing description of the exemplary embodiments of the invention has been presented only for the purposes of illustration and description and is not intended to be exhaustive or to limit the invention to the precise forms disclosed. Many modifications and variations are possible in light of the above teaching. The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope.

What is claimed is:

1. A system for obtaining, processing and managing data from an implanted sensor, the system comprising:
   a flexible antenna comprising a transmit loop and a receive loop, the receive loop for receiving an implanted sensor signal containing data, the transmit loop for transmitting an energizing signal to the implanted sensor, the transmit loop comprising a capacitor to tune the transmit loop, wherein the capacitor is formed by a first element, a second element disconnected from the first element, and a gap between the first element and the second element, the gap having a pre-selected size, wherein the flexible antenna sends the data to a patient device;
   the patient device comprising a patient device engine that creates a data file based on the sensor signal data and transmits the data file to a remote server over the network, wherein the remote server stores the data file; and
   an access device for accessing the data file, wherein the access device is in communication with the remote server.

2. The system of claim 1, further comprising a patient control device associated with the antenna, wherein the patient control device causes the antenna to transmit an energizing signal to the implanted sensor.

3. The system of claim 1, wherein the remote server comprises a management engine that scans the remote server for new data files, formats the data files, and sends a notification to a user that new data files are stored on the remote server.

4. The system of claim 1, wherein the management engine formats the data files by sorting data in a database, generating a waveform based on the data, and creating a visual display of the data.

5. The system of claim 1, wherein the data file comprises patient identification and an implanted sensor signal waveform.

6. The system of claim 1, wherein the transmit loop and the receive loop are associated with a substrate, the substrate being attached to a base comprising a pad adapted to receive a person's body part, wherein the antenna is in communication with the patient device through an antenna cable associated with the base.

7. The system of claim 6, wherein the base comprises self diagnostic circuitry for detecting flexible antenna malfunctions, the self diagnostic circuitry comprising an inductor connected to a capacitor through a switch.

8. A flexible antenna, comprising:
a receive loop that receives implanted sensor signals;
a transmit loop for transmitting an energizing signal to the implanted sensor, the transmit loop comprising a first element, a second element, and a capacitor to tune the transmit loop, wherein the capacitor is formed by the first element, the second element disconnected from the first element, and a gap between the first element and the second element, the gap having a pre-selected size, wherein the flexible antenna sends the data to a patient device; and
a substrate, wherein the receive loop and transmit loop are mounted to the substrate and the substrate being connected to a base.

9. The flexible antenna of claim 8, further comprising a sheath adapted to receive the receive loop and the transmit loop, the sheath being connected to the substrate.

10. The flexible antenna of claim 8, wherein the base comprises:
a pad adapted to receive a person's body part;
a support structure; and
a shield for substantially preventing electromagnetic signals from passing through the shield, the shield comprising a conduit housing an antenna cable adapted to connect to the receive loop and transmit loop.

11. The flexible antenna of claim 10, wherein the pad is a headrest pad adapted to receive a person's head.

12. The flexible antenna of claim 10, wherein the base further comprises self diagnostic circuitry adapted to detect flexible antenna malfunctions, the self diagnostic circuitry comprising an inductor connected to a capacitor through a switch.

13. The system of claim 1, wherein the transmit loop is disconnected from the receive loop.

14. A flexible antenna comprising:
a first loop configured to receive a signal from an implanted sensor, at least part of the signal representing data from the implanted sensor;
a second loop configured to transmit an energizing signal to the implanted sensor, the second loop comprising a first element and a second element, the first element being disconnected from the second element to form a gap having a pre-selected size, wherein the first element and the second element are configured to tune the second loop; and
a substrate in which the first loop and the second loop are mounted, wherein the substrate is connected to a base, wherein the flexible antenna is configured to send the data to a patient device.

15. The flexible antenna of claim 14, wherein the first element and the second element form a capacitor adapted to tune the second loop.

16. The flexible antenna of claim 14, wherein the base comprises self-diagnostic circuitry adapted to detect flexible antenna malfunctions, the self-diagnostic circuitry comprising an inductor connected to a capacitor through a switch.

17. The flexible antenna of claim 14, wherein the base comprises:
a pad adapted to receive a body part of a person;
a support structure; and
a shield for substantially preventing electromagnetic signals from passing through the shield, the shield comprising a conduit that houses an antenna cable adapted to connect to the first loop and the second loop.

18. The flexible antenna of claim 17, wherein the pad is a headrest pad adapted to receive a head of a person.

19. The flexible antenna of claim 17, wherein the base further comprises self-diagnostic circuitry adapted to detect flexible antenna malfunctions, the self-diagnostic circuitry comprising an inductor connected to a capacitor through a switch.

20. The flexible antenna of claim 8, wherein a dielectric material is disposed in the gap.

21. The flexible antenna of claim 8, wherein the gap is formed by at least part of the first element overlapping at least part of the second element.

22. The flexible antenna of claim 21, wherein the first element and the second element each comprise a tubular cross-sectional shape.

* * * * *